United States Patent [19]

Rosskopf et al.

[11] Patent Number: 4,816,162
[45] Date of Patent: Mar. 28, 1989

[54] PROCESS AND DEVICE FOR THE SELECTIVE SEPARATION OF PATHOLOGICAL AND/OR TOXIC SPECIES OR PLASMA

[75] Inventors: Gerhard Rosskopf, Dörnhagen; Dietrich Seidel, Göttingen, both of Fed. Rep. of Germany

[73] Assignee: Intermedicat GmbH, Emmenbrucke, Switzerland

[21] Appl. No.: 744,214

[22] Filed: Jun. 13, 1985

[30] Foreign Application Priority Data

Jun. 16, 1984 [DE] Fed. Rep. of Germany ....... 3422435

[51] Int. Cl.⁴ .............................................. B01D 13/00
[52] U.S. Cl. .................................... 210/651; 210/315; 210/338
[58] Field of Search ............... 210/651, 315, 338, 247, 210/927, 317

[56] References Cited

U.S. PATENT DOCUMENTS

| | | | |
|---|---|---|---|
| 3,542,199 | 11/1970 | Bray et al. | 210/317 X |
| 3,561,602 | 2/1971 | Molitor | 210/317 X |
| 4,000,072 | 12/1976 | Sato et al. | 210/317 X |
| 4,031,010 | 6/1977 | Hose | 210/317 X |
| 4,303,530 | 12/1981 | Shah et al. | 210/651 |
| 4,306,973 | 12/1981 | Ishikawa | 210/336 |
| 4,375,415 | 3/1983 | Lavender | 210/651 |
| 4,472,303 | 9/1984 | Tanihara et al. | 210/927 X |
| 4,490,254 | 12/1984 | Gordon et al. | 210/247 |

OTHER PUBLICATIONS

WO82/03568, Dorson, Jr., et al., 10-1982.

Primary Examiner—Frank Spear
Attorney, Agent, or Firm—Kenyon & Kenyon

[57] ABSTRACT

A process and device for the selective separation of pathological and/or toxic species from blood, plasma or serum wherein a plasma or serum fraction is passed through a container containing one or more filter candles of decreasing means pore diameter and which may contain a sterilizable spacing disc between the filter candles. In accordance with the invention, macromolecular pathological and/or toxic species with molecular weight exclusion limits between about 20,000 and 3,000,000 D may be selectively separated from a fraction of plasma or serum.

29 Claims, 3 Drawing Sheets

FIG.1a
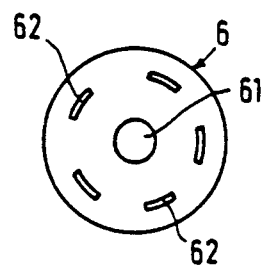
FIG.1b
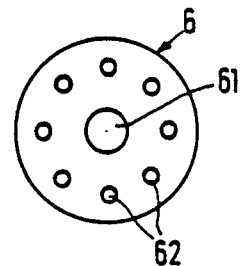
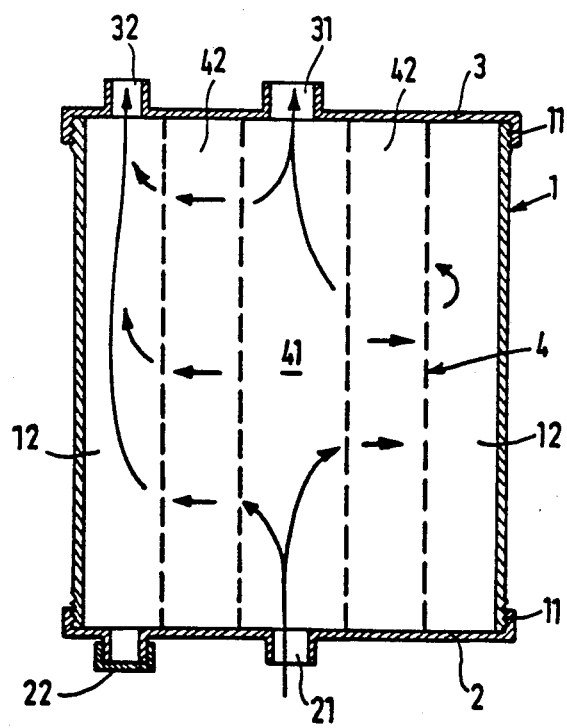
FIG.2

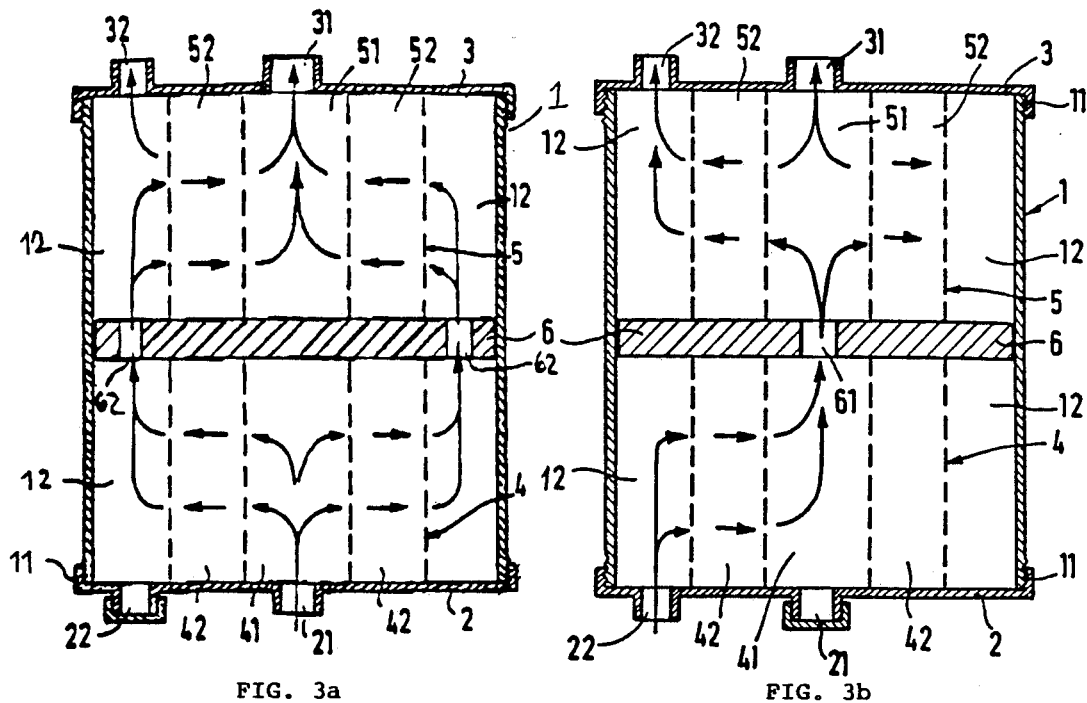
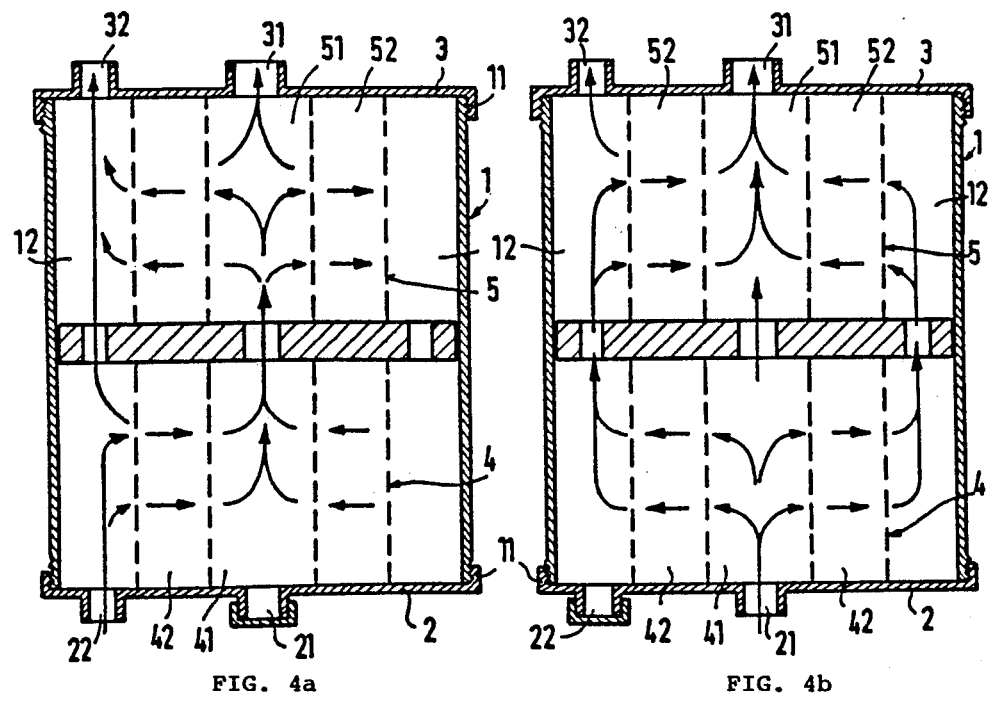

PROCESS AND DEVICE FOR THE SELECTIVE SEPARATION OF PATHOLOGICAL AND/OR TOXIC SPECIES OR PLASMA

BACKGROUND OF THE INVENTION

A current objective in hematology is the largely selective elimination of pathogenic blood or plasma constituents by methods that upset the body as little as possible. For example, a known method of separation is generally performed by passing heparinized blood through the first filter of a cascade consisting of several filters into a stream containing the corpuscular components and a plasma stream, subjecting the latter to a purification process, recombining the purified plasma and the stream containing the corpuscular particles and reinfusing the recombined blood into the patient.

This known process can be carried out in an extracorporeal blood circulation or in stored blood, through the application of an arrangement utilizing the filter cascade for the purpose of the immediate elimination of pathogenic and/or toxic blood or plasma constituents. In the case of stored blood, the blood plasma may also be separated by ultracentrifuge from the corpuscular blood constituents.

The passage of the plasma constituents through the known state of the art membranes is largely dependent on the rate of flow of blood, the transmembrane pressure and the pore size of the membrane used. At present, capillary membrane filters with a pore diameter of approximately 0.2 to 0.5 $\mu$m are suitable to ensure a plasma stream adequate for this process. Capillary membrane filters with a pore size of 0.07 to 0.2 $\mu$m and filter areas of approximately 0.6 m$^2$ are also known, and these may be used as second or third filters of a cascade.

However these known capillary membranes for the treating of the produced plasma stream are disadvantageous in their tendency to form the so-called "secondary membranes" due to protein deposits on their surface. This lowers the membrane permeability rapidly, thereby necessitating the replacement of at least some of the filter element because of the pore occlusion caused by the macroaggregates.

Attempts have been made at keeping the membranes open by pulsating rinses with saline solution during the filtration process, which requires briefly stopping the filtering process and the pumping of rinse solution from a storage vessel through an additional pump and through the filter (H. von Baeyer et al., Trans. Am. Soc. Artif. Intern. Organs 1983: 739). The overloading of the separating system with rinse solution, however, places a great strain on the patient since he receives this solution together with the infusion.

In Applicant's German Offenlegensschrift DE-P 33 10 727.0, a new concept is described for the use of filter candles in plastic containers for the separation of precipitated blood or plasma constituents in extracorporeal circulation systems. The filter candles are characterized by large membrane surfaces at low filling volumes, with pore diameters of the filter candle membranes between 0.2 and 10 $\mu$m. This type of system, which utilizes different filters having different exclusion limits for a filter cascade suitable for the separation of precipitated plasma constituents, is also disadvantageous in that a large part of the patient's blood circulates in the purification cycle and is therefore withheld from the patient's circulation, which, of course, leads to a great strain on the patient. In addition, such a system is unsuitable for the elimination of dissolved plasma constituents.

The combination of different filter units creating a filter cascade in one container makes sense in theory as it reduces the circulating extracorporeal blood volume and is more cost efficient. However, there are limits imposed by the construction on this type of arrangement when using capillary filters since the capillaries are gathered in bundles and cast in polyurethane at the ends. After the polyurethane has set, the fibers are cut off at one end so that they are open at the face side. This makes the combination of several fiber bundles in one container impossible since each individual capillary fiber bundle must be sealed off against the other.

The sealing of each capillary fiber bundle at one side was proposed (Gurland ISAO 1983, Kyoto) as a solution to this problem. This arrangement is disadvantageous in that it can be produced only by complex multi-step procedures and clogging of the stream occurs very quickly in the capillaries' dead zone since the filling volume of the capillaries is very low.

Thus, there exists a need for an effective, relatively simple means by which to separate pathological and/or toxic species from the blood, plasma or serum including dissolved plasma or serum constituents without the development of the so-called secondary membranes which lower membrane permeability.

SUMMARY OF THE INVENTION

It is an object of the present invention to provide a relatively simple means by which to separate pathological and toxic species from the blood, plasma or serum without the development of the so-called secondary membranes which lower membrane permeability.

It is another object of the present invention to provide a process and device for the selective separation of pathological and/or toxic species from blood, plasma or serum utilizing filter candles.

These and other objects are achieved through the provision of a device for the selective separation of pathological and/or toxic species from blood, plasma or serum comprising a container having top and bottom ends which contains one or more filter candles, each filter candle having an effective filter area of about 0.2 to 2 m$^2$ and a series of pores having a mean pore diameter of about 0.015 to 10 $\mu$m.

When two or more filter candles are employed in the container, the filter candles are arranged such that the pore size diameter decreases in the direction of the plasma or serum. The individual filter candles may be separated by a spacing disc compound of a biocompatible, sterilizable material having one or more bores for the channeling of fluids between the filter candles. The device may further comprise within the container an absorber capsule composed of a material that is capable of adsorbing desired constitutents of the blood, plasma or serum.

The invention also contemplates a process for the selective separation of pathological and/or toxic species from blood, plasma or serum which comprises providing a container having top and bottom ends attached by an attachment means and which communicate with intake and outlet nozzles for the conduction of fluids; providing two or more filter candles, each of which has a different exclusion limit and a means pore diameter different from any of the other filter candles and are situated in the container; passing a fraction of plasma or serum containing one or more desired pathological and/or toxic species through one end of the container containing the filter candles such that the fraction traverses the entire length of the container flowing through each filter candle thereby substantially separating out the one or more desired pathological and/or toxic species contained in the plasma or serum; the filter candles being arranged such that the mean pore diameter decreases in the direction of the flow of plasma or serum; and recovering the various plasma fractions including the portion from which the one or more desired pathological and/or toxic species has been separated.

The process further contemplates the step of a recombining with whole blood the recovered fraction from which a substantial portion of the one or more pathological and/or toxic species has been separated and infusing the recombined fraction and whole blood into a subject.

BRIEF DESCRIPTION OF THE DRAWINGS

FIG. 1a illustrates one embodiment of the spacing disc according to the invention.

FIG. 1b illustrates another embodiment of the spacing disc according to the invention;

FIG. 2 illustrates one embodiment of the device according to the invention for the separation of macromolecular constituents from the plasma or serum above a specified molecular weight employing a filter candle;

FIG. 3 (a) and (b) illustrates other embodiments of the device according to the invention for the separation of macromolecular constituents from the plasma or serum above a specified molecular weight and subsequent fractionation of the filtrate employing a combination of two filter candles, with the residue of the "prefilter" remaining in the filter candle;

FIG. 4 (a) and (b) illustrate embodiments of the device according to the invention for the fractionation of plasma or serum into several reclaimable fractions employing a combination of two filter candles;

DETAILED DESCRIPTION OF THE INVENTION

Figure 5:
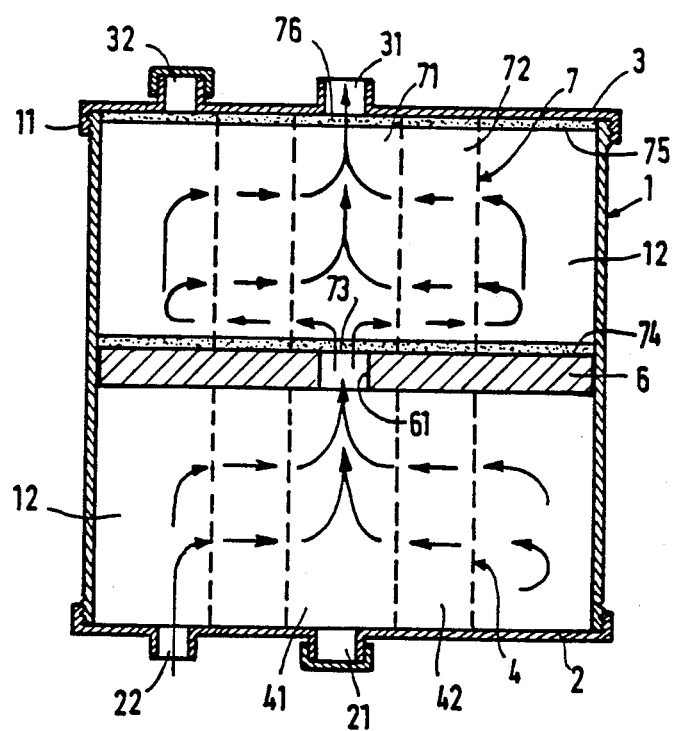
FIG. 5 illustrates another embodiment according to the invention for the separation of fraction of the plasma or serum with the user of a filter candle and subsequent additional purification of the filtrate employing a capsule filled with an adsorbent material.

The invention concerns a process and device for the selective separation of macromolecular pathological and/or toxic blood constituents from whole blood, plasma or serum with the use of an apparatus employing one or more filter-candles.

It has now been surprisingly observed that plasma or serum filters in which filter candles are employed as a separation means not only eliminate precipitates of solid or gel-like consistency from the blood plasma or serum but also separate out dissolved pathogenic constitutents from the blood plasma or serum when filter candles with a mean pore diameter in the range of about 0.015 to 10 $\mu$m are employed in plastic or glass containers.

It has also been surprisingly observed that dissolved pathogenic blood constituents with a mean molecular weight anywhere in the range of the molecular weights of all the constituents present in the plasma or serum can be eliminated from the plasma or serum by employing filter candles in a plastic or glass container whose respective means pore diameters are chosen according to the size of the dissolved pathogenic blood constituents sought to be eliminated. Consequently, the separation of dissolved pathogenic constituents of a predetermined molecular weight range does not cause other constituents with mean molecular weights higher or lower than the predetermined molecular weight to be retained as well, which permits the recombining, as filtrate, of these other constituents having a higher or lower mean molecular weight with the corpuscular blood constituents. The reinfusion of this recombined blood in the patient is then possible.

The preferred embodiment of the invention concerns the use of one or more filter candles having an effective filter area between about 0.2 and 2 $m^2$, a length of about 10 to 50 cm as well as a mean pore diameter between about 0.015 and 10 $\mu$m in sterilizable plastic or glass containers for the selective separation of macromolecular species from blood or constituents of the blood such as whole serum or plasma. When more than one filter candle is employed, two or more successive filter candles may be separated by a spacing disc of a biocompatible, sterilizable plastic that has several bores for the conduction of liquids, with the filter candles distinguished by a decreasing mean pore diameter.

Thus, in accordance with the invention, macromolecular pathological and/or toxic species from the blood or constituents of the blood such as whole serum or plasma with molecular weight exclusion limits between about 20,000 and 3,000,000 D may be selectively separated from a plasma or serum fraction of a patient's blood, stored blood or fractions thereof produced by conventional means such as a capillary or membrane plasma filter or the last filter of a cascade assembly of several such filters. The plasma or serum fraction may be led without pressure thorough a sterilized plastic or glass container having one or more filter candles. When more than one filter candle is employed, two successive filter candles may be separated by a spacing disc of a biocompatible, sterilizable material having several bores for the conduction of liquid.

The pores of the filter candle material cause a separation of the plasma or serum constituents according to the molecular mass and the molecular shape of the constituents, and the fractions separated by this method are drained through various outlet nozzles of the container. The desired fractions, after the separation of excess reagents and the adjusting of the fractions to physiological conditions, e.g., pH, may then be combined with the blood, plasma or serum stream from the preceding filter and returned to the patient by reinfusion.

The device according to the invention for the selective separation of fractions of macromolecular pathological and/or toxic species from the blood or blood constitutents such as whole serum or plasma, which constituents are preferably produced by the addition of chemical reagents and/or by elevating or lowering the temperature, comprises a sterilizable, preferably cylindrical plastic or glass container having a screw thread or some other attaching means at the upper and/or lower container ends and a bottom and top compatible with the ends, each equipped with a centrally and/or tangentially attached intake nozzle and a centrally and/or tangentially attached outlet nozzle, and which contains one or more filter candles each having, in preferred embodiments, an effective filter area between about 0.2 and 2 $m^2$ each, a length of about 10 to 50 cm as well a a mean pore diameter between about 0.015 and 10 $\mu$m. When more than one filter candle is employed, the individual filter candles may be separated by a spacing disc composed of a biocompatible, sterilizable plastic having several bores for the conduction of liquid. The bottoms and tops of the filter candles are connected with the bottoms and tops of the container as well as with the intake and outlet nozzles of the container.

A preferred practical example of the device according to the invention employs "NUCLEOPORE QR ®" filter candles for the filtration of the plasma or serum, which contains a filtration medium consisting of a polycarbonate membrane and which has a filter area between about 0.2 and 2.0 m² per filter candle and a length of about 24.8 to 50.2 cm per filter candle. However, any other filter candle meeting the stated requirements may be employed in the invention as well.

The "NUCLEOPORE QR ®" filter candles has, depending on the type, pore sizes in the range about 0.015 to 10 μm. Its use is particularly advantageous since the relative scatter of its pore sizes is below 20% due to the method by which it is produced, which utilizes nuclear track technology and an etching process.

A selection of the pore size of the filter candles for the plasma or serum fractionation solely in accordance with molecular weights of the toxic and/or pathological species to be eliminated from the plasma is impossible since the plasma constituents that are to be separated (cf. Table 1 below) are not exclusively spherical in shape. Empirical values of the pore size of a filter candle suitable in an individual case can be determined by simple pilot experiments known to a person skilled in the art, so far as they are covered by the range of values of the present invention.

TABLE 1

Toxic and/or pathological species in the blood plasma, which are to be separated.

| Species | MW($10^3$D) |
|---|---|
| Bence-Jones bodies | 25 |
| Albumin | 68 |
| IgA | 150 |
| IgG | 160 |
| Beta-2-Macroglobulin | 725 |
| IgM | 950 |
| Beta-Lipoprotein | 2,400 |

Consequently, one advantage of the present invention which employs filter candles for the separation of certain species from the blood plasma is that even when two different species have a mean molecular weight on the same order of magnitude, a separation or removal from the plasma of one of the two species can be effectuated by choosing the pore size or the pore size gradient of a filter candle combination in such a manner that may be specifically adapted to the separation of one species from the other species. Thus, almost quantitative removal of the respective species from the plasma or serum is made possible by the invention even in the case where other species of higher and/or lower mean molecular weights are present in the plasma.

In a preferred embodiment of the invention, the first filter candle used in a combination of filter candles is one with relatively large pores, e.g., in the range of about 0.2 to 10 μm. The "wide" first filter candle thus serves as a prefilter that makes the removal of aggregates of higher molecular weight species possible which otherwise clog the following filter candles which have considerably smaller pore sizes. The filtrate flowing from this prefilter is then separated by a second filter candle, while the residue is discarded if it also contains undesirable components. In the alternative, the residue can be recombined with the purified plasma if it does not contain any undesirable toxic and/or pathogenic components.

Yet another advantage of employing filter candles in the device according to the inveniton is that the release of any possibly toxic species during the filtration process that could be returned to the blood circulation possibly causing damage to the subject is minimized or eliminated. The materials used therein are contemplated to meet the highest demands for sterility and asepsis.

The filter candles employed in accordance with the invention are placed in sterilizable containers of plastic or glass, which preferably consist of a cylindrical body and two covers with intake and outlet nozzles. The length of the container depends on the number of filter candles used; the length should be chosen to accommodate one or more filter candles together with any spacing and connecting means such as spacing discs which separate the individual compartments and permit the outside top and outside bottom area of the filter candle(s) to be tightly connected to the cap or bottom of the plastic or glass container.

In the preferred embodiment of the device according to the invention, the hollow interior of the filter candle or candles employed is altered by the insertion of a solid or partly solid body, which is preferably cylindrical in shape. This body accomplishes a distinct reduction in the fluid capacity of the filter candle or candles thereby maintaining the amount of volume in the device according to the invention to a minimum, without impairing the function of the filter candles. Moreover, this embodiment has the additional effect of guiding the plasma flow toward the filter surfaces or the outlet nozzles of the container.

In accordance with the invention, when two or more filter candles are employed, which are arranged in combination in a container, they are separated from one another by plastic discs consisting of a biocompatible, sterilizable plastic. These spacing discs have a diameter corresponding to the inside diameter of the plastic or glass container, and they serve to separate the filtration space of the first filter candle from the filtration space of the subsequent filter candle(s).

Ideally, the spacing discs have an inside bore, preferably circular in shape, with a diameter largely corresponding to the inside diameter of the central inner space of the filter candles employed. This inside bore is intended as a channel for the filter residue that does not pass through the pores of the first filter candle because of its high molecular weight and/or its molecular form. A preferred embodiment of the spacing disc has a relatively narrow inside bore that allows only a small volume of the total plasma to pass, while guiding the main volume, which contains the constitutents with lower molecular weight, through the filter medium of the first filter candle.

The mentioned spacing discs are of a biocompatible, sterilizable plastic and have several slit-like or point-like openings between the inside bore and the outer edge that makes the passing of the plasma filtrate draining from the first filter candle to the second filter candle possible. The number of slit-like or point-like openings is variable and depends on the rate of flow of the plasma filtrate; it is preferably in the range of 3 to 5.

Preferred practical examples of the spacing discs are illustrated in FIGS. 1a and 1b.

In another practical example of the invention, one of the two filter candles separated by a spacing disc illustrated in FIG. 1 can be replaced by an adsorption filter cartridge, which consists of a solid or hollow core and a support screen around which a fiber mat on a cellulose base acting as an active adsorbent is wound, or by an analogously geometrically shaped container of the same dimensions that contains a filter medium or adsorption medium and screens at the intake and outlet to prevent the release of particles while permitting the passing of plasma or serum. Furthermore, one of the two filter candles itself can be equipped with an active adsorber material. This may be significant, for example, if pathological and/or toxic blood constituents are to be removed from whole blood, plasma or serum as well as larger amounts of natural and/or synthetic compounds such as heparin.

For this purpose, the device according to the invention can also be coupled, in the form described above, with other elimination systems, e.g., adsorbers. The process according to the invention for the selective separation of macromolecular pathological and/or toxic species from blood, plasma, or serum is explained in further detail with reference to FIGS. 2 to 4 below.

The process variants described in FIGS. 3 and 4 can also be carried out analogously by employing a number of filter candles larger than two.

The container 1 of plastic or glass shown in Figure 2 contains a filter candle with ends closely connected to bottom 2 and top 3 of containers 1 for the separation of a fraction of macromolecular constituents from blood plasma (hereinafter referring to plasma or serum) with molecular weights above a selected molecular weight limit. The pore size of filter candle 4 is selected so that it falls within the lower range of the molecular weights that are to be separated from the blood plasma.

The plasma can flow toward filter candle 4 installed in container 1 either from the outside or the inside, with the stream of plasma flowing from bottom 2 of the container toward top 3. In the former case, the plasma to be filtered is guided through the central intake nozzle 21 to container 1, while the tangential intake nozzle 22 is closed. Plasma constituents with molecular weights above the exclusion limit of the filter candle do not enter filtration space 42 of the filter candle 4 but are guided through central inner space 41 of the filter candle to central outlet nozzle 31. Plasma constituents with mean molecular weights below the exclusion limit of the filter candle pass through filtration space 42 and reach space 12 between filter candle 4 and container wall, where they are guided toward tangential outlet nozzle 32.

The one or other fraction can then optionally be fed through central intake nozzle 21, as desired, for another filtration of the respective plasma portion.

In the case of a flow toward the filter candle from the inside surface, the plasma is fed through tangential intake nozzle 22 into container 1, while central intake nozzle 21 is closed. The low molecular weight portions of the plasma pass through filtration space 42 of filter candle 4 and reach inner space 41, from where they are led toward central outlet nozzle 31, while the higher molecular weight portions in space 12 between filter candle 4 and the container wall are guided toward tangential outlet nozzle 32. A recirculation of one of the two fractions is also possible in this case.

In the embodiment of the device according to the invention shown in FIG. 3 (a) and (b), two filter candles 4 and 5 are arranged in a container 1 in which the bottom of first filter candle 4 and the top of the second filter candle 5 form a tight closure with bottom 2 and top 3 of the plastic or glass container 1. Both filter candles are separated by a spacing disc 6 of a biocompatible, sterilizable plastic material, which has either a central bore 61 as depicted in FIG. 3 (b) or several peripheral bores 62, as depicted in FIG. 3 (a).

In the conception of the device according to the invention depicted by FIG. 3 (a) and (b), the first filter candle 4 serves as a prefilter, which removes macromolecular plasma constituents to prevent a clogging of the pores of the second filter candle 5 that has a considerably smaller pore size.

The components prefiltered by the first filter candle 4 remain in the prefilter, while the second filter candle 5 serves to fractionate the filtrate of filter candle 4 into two fractions.

As the fluid plasma flows toward the filter surface of the first filter candle 4 from the inside as depicted in FIG. 3 (a), it is guided to the container through central intake nozzle 21, while tangential intake nozzle 22 is closed. "Prefilter" 4 filters out the macromolecular constituents of the plasma, which remain in the inner space 41, while the low molecular weight constituents easily penetrate filtration space 42 and reach space 12 between filter candle 4 and the container wall. Through the peripheral bores 62 of spacing disc 6 the filtrate reaches the space between filter candle 5 and the container wall, where it flows towards the second filter candle 5 from the outside. Plasma constituents with moelcular masses above the exclusion limit of filter candle 5 do not penetrate into filtration area 52 of filter candle 5, but are removed through tangential outlet nozzle 32. Plasma constituents with mean molecular weights below the exclusion limit of filter candle 5 penetrate filtration area 52 of filter candle 5 and reach inner space 51, from where they are led to central outlet nozzle 31 of container 1 and drawn off there. A recirculation of the component drawn off at tangential outlet nozzle 32 is again possible. The macromolecular plasma constituents remaining in inner space 41 are discarded together with filter candle 4.

Again, a flow toward the first filter candle from the outside as shown in FIG. 3 (b) is also possible as an alternative, whereby the plasma is guided into container 1 through tangential intake nozzle 22, while central intake nozzle 21 is closed. The high molecular weight plasma constituents remain in space 12 between filter candle 4 and the container wall, while the low molecular weight constituents penetrate filtration area 42 of filter candle 4 and reach inner space 41. There they are led through a central bore 61 in spacing disc 6 into inner space 51 of filter candle 6, where the higher molecular weight fraction is drawn off through central outlet nozzle 31 and, if needed, recirculated, while the low molecular fraction penetrates filtration area 52 of the second filter candle 5, reaches space 12 between filter candle 5 and the container wall and is drawn off through tangential outlet nozzle 32.

FIG. 4b shows a practical example of the device according to the invention for the fractionation of plasma into several recoverable fractions by employing a combination of two filter candles. The plasma to be fractionated is led into container 1 through central intake nozzle 21, while tangential intake nozzle 22 is closed. The plasma flows toward the first filter candle 4 from the inside. The fraction with mean molecular weights above the exclusion limit of first filter candle 4 remain in inner space 41 of the first filter candle 4, while the fraction with species having a lower mean molecular weight than the exclusion limit of filter candle 4 reach space 12 between candle 4 and the container wall through filtration area 42 of filter candle 4, and penetrate there through peripheral bores 62 of spacing disc 6 into space 12 between filter candle 5 and the container wall. The portions of the plasma that have a higher mean molecular weight than the exclusion limit of second filter candle 5 do not penetrate into filtration area 52 of filter candle 5, but are led through tangential outlet nozzle 32 from the container 1 and can, if needed, be recirculated by being added to the plasma stream that is fed in by recirculation. The plasma constituents with a mean molecular weight below the exclusion limit of second filter candle 5 penetrate filtration area 52 of filter candle 5 and reach inner space 51, where they are combined with the plasma portion of the highest molecular weight constituents flowing through central bore 61 and are drawn off from container 1 through central outlet nozzle 31. This fraction is then combined with the corpuscular constituents of the blood and returned to the patient by infusion.

Another embodiment of the invention is a process depicted in FIG. 4a, in which the flow toward the first filter candle 4 is directed from the outside and toward the second filter candle 5 from the inside. The purified plasma fractions are drawn off in this case through tangential outlet nozzle 32, while the pathological and/or toxic species is removed from container 1 through central outlet nozzle 31.

The desired fractions which can be drawn off from central outlet nozzle 31 or tangential outlet nozzle 32, are then, if needed, freed of excess reagents and, after dialysis against a suitable solution, which preferably is a bicarbonate dialysis which adjusts the pH to a natural 7.4, is combined with the portion of whole blood containing the corpuscular constituents from the preceding filter and returned to the patient by infusion.

Table 2 below contains examples of possible filter combinations, with filter numbers 4 and 5 corresponding to filter candles 4 and 5 in FIGS. 3 and 4. It is apparent from the second column that the first filter candle 4 always has a pore size above the pore size of the following filter candle 5 of the filter candle combination.

TABLE 2

| Filter | Exclusion limit | Therapeutic objective |
|---|---|---|
| 4 | $M_w$ 1,000,000 D | Separation of the spectrum of the immune globulins IgM, IgG and IgA, circulating immune complexes |
| 5 | $M_w$ 100,000 D | |
| 4 | $M_w$ 250,000 D | Separation of IgG and IgA |
| 5 | $M_w$ 100,000 D | |
| 4 | $M_w$ 50,000 D | Separation of Bence-Jones proteins |
| 5 | $M_w$ 20,000 D | |
| 4 | 10μ | Prefilter for the prevention of clogging pores and separation of IgM |
| 5 | 0.2μ | |

The process described above, which can be carried out in the extracorporeal circulation as well as "off-line" with stored blood, is normally performed at normal body temperature. However, process variants requiring a filtration at temperatures below body temperature down to about 0° C. are conceivable. In this case, the cylindrical plastic or glass container is enclosed in a thermostatic jacket that is cooled with a liquid, preferably water. The process can also be performed analogously at temperatures above body temperature up to about 60° C. In this case, the mentioned thermostatic jacket is heated, preferably with water, to the necessary temperature. The cylindrical plastic or glass container can also be heated by heating wires enclosed in the container wall. In a preferred practical example of the device according to the invention, the container wall contains, in addition to the mentioned heating wires, contact pins allowing a temperature regulation by a monitor.

FIG. 5 shows a practical example of the device according to the invention for the separation of the plasma with the use of a filter candle and subsequent adsorption of one of the filtrate components in an adsorber capsule arranged in combination with the filter candle. The plasma to be purified is led through tangential intake nozzle 22 into container 1, while central intake nozzle 21 remains closed. The plasma flows toward filter candle 4 from the outside. This filter candle can be used, e.g., for the separation of beta-lipoproteins from the solution, which were precipitated by treating with heparin or one of its derivatives as described in German Offenlegensschrift P 34 22 407.6. Filter candle 4 must have a pore size between about 0.2 and 2.0 μm for this purpose.

The precipitate remains in space 12 between filter candle 4 and the container wall, while the filtrate containing heparin reaches inner space 41 through filtration area 42 of filter candle 4 and flows from there, through central bore 61 of spacing disc 6, and into intake nozzle 73 of adsorber capsule 7. The filtrate is led through the medium that adsorbs heparin, contained in adsorber capsule 7. Here, heparin and/or its derivatives are specifically adsorbed in adsorber area 72 of adsorber capsule 7, while the remaining plasma components can be drawn off through outlet nozzle 76 of the adsorber capsule and central outlet nozzle 31. Double screens 74 and 75 having a predetermined mesh, e.g., 100 μm mesh, are inserted in the top of adsorber capsule 7 equipped with central intake nozzle 73 and outlet nozzle 76 to prevent the release of particles.

Another practical example of the invention includes the combination of the described filtration process using one or more filter candles together with other filtration methods. In one such case, other filtering media can be interconnected before or behind the arrangement according to the invention in which specific species are to be separated from the plasma by the use of filter candles, and the process may take place in an extracorporeal circulation as well as with stored whole blood or plasma prepared and conditioned by known methods.

For example, an additional removal of heparin and/or its derivatives and be carried out in one filtration passage by connecting an adsorber capsule containing a heparin-adsorbing medium, e.g. an adsorption filter cartridge, consisting of a solid or hollow core and a supporting screen around which there is a fiber mat on a cellulose base having anion exchanger characteristics. The result is that an active adsorbent is wound in front of or behind the device containing one or several filter candles.

If the adsorber capsule is connected in front of the device containing filter candles, the blood or plasma to be purified is first led over the adsorber medium, which results in a selective adsorption of, e.g., heparin and/or its derivatives; then, the deheparinized fluid passes through the container with one or more filter candle(s), through which a purification according to the process described above is accomplished. When the adsorber capsule is connected behind the container holding the filter candles, the separation process described above with the use of the filter candles is carried out first, after which the fluid is led over the medium in the adsorber capsule and the species sought to be adsorbed, e.g., heparin and/or its derivatives, is specifically adsorbed. The placing of the adsorption filter cartridge in front of the container holding the filter candles is not recommended if the species to be filtered out would clog the adsorption filter cartridge because of its size.

Instead of loading the adsorber capsule with an adsorption filter cartridge, capsules filled with other adsorbing materials, e.g., resins or gels, can be employed as well.

The invention is explained in more detail by the following examples.

EXAMPLE 1

Separation of IgM from Stored Whole Blood

Whole blood from stored blood was separated into corpuscular constituents and plasma by the use of a commercial capillary filter with 0.5 $\mu$m pore size, while a blood stream of 100 ml/min was maintained with the aid of a pump. The resulting plasma was led into a container having a filter candle at a rate of approximately 40 ml/min. The filter candle had a diameter of 7 cm, a length of 24.5 cm and an effective filter area of 1.7 m$^2$. The filter material had a pore diameter of 0.1 $\mu$m.

The plasma was tested for its content of immunoglobulin M (IgM, MW approximately 950,000 D) before entering and after leaving the filtration cycle. The tests showed that 95% of the IgM was separated in the filtrate.

EXAMPLE 2

Separation of Immunoglobulin A and

Immunoglobulin G from the Stored Plasma

Plasma from stored plasma was led into a container with two filter candles, the first with a length of 10 cm and a pore size of 0.1 $\mu$m, the second with a length of 10 cm and a pore size of 0.02 $\mu$m, with the aid of a pump at a rate of flow of 60 ml/min for the separation of immunoglobulin A (IgA, MW approximately 150,000 D) and immunoglobulin G (IgM, Mw approximately 160,000 D).

The plasma was tested for its content of IgA and IgG before entering and after leaving the filtration container. The content of the two immunoglobulins was reduced to 20% of its initial value after the completion of the filtration.

EXAMPLE 3

Separation of Beta-Lipoprotein-Heparin Complex Precipitated by Addition of Heparin and Dehararinization of the Plasma Whole blood was freed of corpuscular constituents by running through a capillary filter with a pore size of 0.5 $\mu$m. Beta-lipoprotein was precipitated in the remaining plasma by the addition of heparin. The precipitate was fed into a container with one filter candle (pore size: 0.2 $\mu$m), a spacing disc of a biocompatible plastic material and an adsorber capsule containing a "ZETA-PREP ®" 250/1 fiber mat. A rate of flow of 60 ml/min was maintained with the aid of a pump.

The plasma was tested for its content of beta-lipoproteins and its content of heparin, after removal from the container. The beta-lipoproteins were found to have been completely precipitated and separated, while the heparin content had been reduced to 1% of its initial value.

No adsorption of other proteins on the fiber mat could be determined.

While there have been described what are presently believed to be preferred embodiments of the invention, it will be apparent to a person skilled in the art that numerous changes can be made in the ingredients, conditions and proportions set forth in the foregoing embodiments without departing from the invention as described herein and as defined in the appended claims.

What is claimed is:

1. A device for the selective separation of pathological and/or toxic species from blood, plasma or serum comprising a container having a bottom end with at least two outlet nozzles for the draining of separated plasma or serum constituents and a top end with at least one intake nozzle and which contains at least a first and a second cylindrical filter, each filter having an effective filter area of about 0.2 to 2 m$^2$ and a series of pores having a mean pore diameter of about 0.015 to 10 microns; said filters being arranged in series about a central inner space so that the blood plasma or serum flows through the first filter and then through the second filter and the pore size diameter of the first filter being greater than that of the second filter such that the pore size diameter decreases in the direction of flow of the plasma or serum.

2. The device according to claim 1 further comprising an adsorber capsule composed of a material that is capable of adsorbing desired constituent(s) of the blood, plasma or serum.

3. The device according to claim 2 wherein the adsorber capsule comprises a fiber mat on a cellulose base that acts as an adsorbent which is wound on a supporting screen around a solid or hollow core and possesses ion exchange characteristics.

4. The device according to claim 1 wherein the individual filters are separated by a spacing disc composed of a biocompatible, sterilizable material having one or more bores for the channeling of fluids between the filters.

5. A process for the selective separation of pathological and/or toxic species from blood, plasma or serum which comprises passing a plasma or serum fraction through a plastic or glass container having at least one intake nozzle and at least two outlet nozzles for the draining of separated plasma or serum constituents and containing at least two cylindrical filters arranged in series each about a central inner space having a filtering surface of about 0.2 to 2 m$^2$ and a mean pore diameter between about 0.15 and 10 microns, such that the plasma or serum fraction flows through the intake nozzle, traverses the filters and exits through the outlet nozzles.

6. A device for the selective separation of pathological and toxic species from the blood, plasma or serum comprising:
 (a) an intake nozzle;
 (b) a container connected at one end to the intake nozzle having top and bottom ends attached by an attachment means;
 (c) at least a first and a second filter candle contained in the container each having an effective filter area of about 0.2 to 2 m$^2$ and a series of pores having a mean pore diameter of about 0.015 to 10 μm, with the mean pore diameter of the first filter candle being different from the second filter candle; the filter candles being arranged in series each about a central inner space with the first filter candle being situated upstream of the second filter candle and the pore size diameter of the first filter candle being greater than that of the second filter candle;

(d) a spacing disc situated between the filter candles which is composed of a biocompatible, sterilizable material having one or more bores for the channeling of fluid;

(e) an outlet nozzle connected to the container at the other end of the container closest to the second filter candle.

7. The device according to claim 6 further comprising within the container an adsorber capsule composed of a material that is capable of adsorbing desired constituents of the blood, plasma or serum.

8. The device according to claim 7 wherein the absorber capsule comprises a fiber mat on a cellulose base that acts as an active adsorbent which is wound on a supporting screen around a solid or hollow core and possesses ion exchange characteristics.

9. The device according to claim 6 wherein a solid or partly solid body is situated in an inner space of the one or more of the filter candles thereby reducing the filling volume of the container.

10. A process for the selective separation of pathologically and/or toxic species from blood plasma or serum which comprises the steps of:

(a) providing a container having top and bottom ends connected by longitudinal walls, and which communicate with intake and outlet nozzles for the conduction of fluids;

(b) providing at least a first filter candle and a second filter candle in the container situated to form a space between each filter candle and the container wall, each of which having an exclusion limit and a mean pore diameter different from any of the other filter candles;

(c) passing a fraction of plasma or serum containing one or more desired pathological and/or toxic species through one end of the container containing the filter candles such that the fraction traverses the entire length of the container, flowing through each filter candle thereby substantially separating out the one or more desired pathological and/or toxic species contained in the plasma; the filter candles being arranged in series each about a central inner space such that the mean pore diameter decreases in the direction of the flow of the plasma or serum; and (d) recovering the various plasma fractions including the portion from which the one or more desired pathological and/or toxic species has been separated.

11. The process according to claim 10 further comprising the step of recombining the recovered plasma or serum fraction from which the one or more desired pathological and/or toxic species has been separated with whole blood and infusing the recombined plasma or serum and whole blood into a subject.

12. The process according to claim 10 wherein each filter candle is separated from another filter candle by a spacing disc composed of a biocompatible sterilizable material having one or more bores for the channeling of fluid.

13. The process according to claim 10 wherein a solid or partly solid body is situated in an inner space of one or more of the filter candles thereby reducing the filling volume of the container.

14. The process according to claim 10 further comprising an adsorber capsule contained in the container along with the filter candles and which is composed of a material that is capable of adsorbing desired pathological and/or toxic species from the fraction.

15. The process according to claim 14 wherein the adsorber capsule comprises a fiber mat on a cellulose base that acts as an active adsorbent and which is wound on a supporting screen around a solid or hollow core and possesses ion exchange characteristics.

16. The process according to claim 10 wherein the fraction of plasma is passed through the container without pressure.

17. The process according to claim 10 wherein the portion of plasma or serum from which the pathological and/or toxic species has been separated is drawn off from the container through a outlet different from that through which a fraction containing the pathological and/or toxic species is drawn.

18. The process according to claim 10 wherein the plasma or serum flows toward the filter candle surface from the inside of the filter candle, the plasma or serum portion having constituents with molecular weights above the exclusion limit of the first filter candle continuing to flow as a first fraction through a connecting means into the second filter candle, while the portions having constituents with molecular weights below the exclusion limit of the first filter candle flow, as filtrate, into the space between the first filter candle and the container wall, and which continues to flow through a second connecting means into the space between the container wall and the second filter candle, wherein the constituents having molecular weights below the exclusion limit of the second filter candle flow, as a filtered third fraction, into the inner space of the second filter candle, while the constituents having molecular weights above the exclusion limit of the second filter candle remain, as the second fraction, in the space between the container and the second filter candle, from where said second fraction is transferred for additional filtration steps, if necessary, and the remaining fractions are removed through various outlet nozzles of the container.

19. The process according to claim 10 wherein the plasma or serum flows toward the filter surface from the inner space of the first filter candle, plasma or serum constituents having molecular weights above the exclusion limit of the first filter candle continue to flow as a first fraction in the inner space of the first filter candle, through the connecting means and into the inner space of the second filter candle, while constituents with molecular weights below the exclusion limit of the first filter candle reach the space between the first filter candle and the container wall as filtrate, continue flowing through a second connecting means into the space between the container wall and the second filter candle, wherein the constituents with molecular weights below the exclusion limit of the second filter candle flow as a filtered third fraction into the inner space of the second filter candle, while constituents with molecular weights above the exclusion limit of the second filter candle remain as the second fraction in the space between the container wall and the second filter candle; the combined first and third fractions being removed through an outlet nozzle connecting with the inner space of the second filter candle, and the second fraction being removed through a tangentially located outlet nozzle connecting with the space containing the second fraction.

20. The process according to claim 10 wherein the plasma or serum flows towards the filter surface of the first filter candle from the outside, plasma or serum constituents having molecular weights above the exclusion limit of the first filter candle continue to flow as a first fraction in the space between the first filter candle and the container wall, while plasma or serum constituents with molecular weights below the exclusion limit of the first filter candle reach the inner space of the first filter candle as filtrate, which flows through the connecting means connecting the inner space of the first and second filter candles and into the inner space of the second filter candle, where constituents with molecular weights above the exclusion limit of the second filter candle remain as a second fraction, while constituents with molecular weights below the exclusion limit of the second filter candle pass into the space between the second filter candle and the container wall as a third fraction; the combined first and third fractions being removed through a tangential outlet nozzle in connection with the space between the second filter candle and the container, and the second fraction being removed through a central outlet nozzle in connection with the inner space of the second filter candle.

21. The process according to claim 10 wherein the exclusion limits of the filter candles is between about 20,000 and 3,000,000 D.

22. The process according to claim 10 wherein two filter candles having exclusion limits of about 50,000 and 20,000 D are employed.

23. The process according to claim 10 wherein two filter candles having exclusion limits of about 250,000 and 100,000 D are employed.

24. The process according to claim 10 wherein two filter candles having exclusion limits of about 1,000,000 and 100,000 D are employed.

25. The process according to claim 10 wherein the filter candles have exclusion limits between about 20,000 and 1,000,000 D.

26. The process according to claim 10 wherein each of the filter candles has a filtering surface between about 0.2 and 2 $m^2$ and a mean pore diameter between about 0.015 and 10 $\mu m$.

27. A process for the selective separation of pathological and toxic species from blood, plasma or serum which comprises the steps of:
(a) providing a container having top and bottom ends attached by longitudinal walls and intake and outlet nozzles in connection therewith;
(b) at least a first and a second filter candle arranged in series in the container each about a central inner space and each of which having a filtering surface of about 0.2 to 2 $m^2$ and a mean pore diameter between about 0.015 and 10 microns, each having an exclusion limit and a mean pore diameter different from any of the other filter candles, and each being connected to another by a spacing disc having one or more bores for the conduction of fluids;
(c) passing a fraction of plasma or serum through one end of the container containing the filter candles such that the fraction flows through the entire length of the container and flows through each filter candle thereby separating out a substantial portion of the one or more pathological and/or toxic species contained in the plasma or serum; the filter candles being arranged such that the pore size diameter and exclusion limit of each successive filter candle decreases in the direction of the flow of the fraction;
(d) recovering the various fractions including the portion from which all or most of the one or more pathological and/or toxic species has been separated.

28. The process according to claim 27 further comprising the step of recombining with whole blood the recovered fraction from which a substantial portion of the one or more pathological and/or toxic species has been separated and infusing the recombined fraction and whole blood into a subject.

29. The process according to claim 27 further comprising an adsorber capsule which is contained in the container along with the filter candles and which is composed of a material that is capable of adsorbing desired pathological and/or toxic species from the fraction.

* * * * *

UNITED STATES PATENT AND TRADEMARK OFFICE
CERTIFICATE OF CORRECTION

PATENT NO. : 4,816,162

DATED : March 28, 1989

INVENTOR(S) : Gerhard Rosskopf, et al.

It is certified that error appears in the above-identified patent and that said Letters Patent is hereby corrected as shown below:

In the abstract, line 5, delete "means" and substitute therefor --mean--.

Column 2, line 65, delete "means" and substitute therefor --mean--.

Column 3, line 42, delete "user" and substitute therefor --use--.

Column 3, line 67, delete "means" and substitute therefor --mean--.

Column 8, line 52, delete "6" and substitute therefor --5--.

Column 11, line 57, delete "Dehararinization" and substitute therefor --Deheparinization--.

Column 13, lines 29-30, delete "pathologically" and substitute therefor --pathological--.

Column 14, line 21, delete "a" and substitute therefor --an--.

Signed and Sealed this

Ninth Day of January, 1990

Attest:

JEFFREY M. SAMUELS

*Attesting Officer*   *Acting Commissioner of Patents and Trademarks*